United States Patent [19]
Murray

[11] Patent Number: 6,096,676
[45] Date of Patent: Aug. 1, 2000

[54] CATALYST FOR THE PRODUCTION OF OLEFIN POLYMERS

[75] Inventor: Rex Eugene Murray, Charleston, W. Va.

[73] Assignee: Union Carbide Chemicals & Plastics Technology Corporation, Danbury, Conn.

[21] Appl. No.: 09/099,856

[22] Filed: Jun. 18, 1998

Related U.S. Application Data

[60] Provisional application No. 60/051,522, Jul. 2, 1997.
[51] Int. Cl.$^7$ .......................... C01G 25/00; C01G 25/04; C01G 23/00; C01G 23/02; C01G 27/04
[52] U.S. Cl. .......................... 502/117; 502/123; 502/155; 556/52; 556/56
[58] Field of Search ................................ 502/117, 123, 502/155; 556/52, 56

[56] References Cited

U.S. PATENT DOCUMENTS

| | | | |
|---|---|---|---|
| 5,318,935 | 6/1994 | Canich et al. | 502/117 |
| 5,707,913 | 1/1998 | Schlund et al. | 502/102 |

FOREIGN PATENT DOCUMENTS

| | | |
|---|---|---|
| 0320169A2 | of 1989 | European Pat. Off. . |
| 0349886 | of 1990 | European Pat. Off. . |
| 0509233A2 | of 1992 | European Pat. Off. . |
| 761694 | 3/1997 | European Pat. Off. . |
| 0803520A1 | 4/1997 | European Pat. Off. . |
| 4202889 | 8/1993 | Germany . |
| 9212162 | of 1992 | WIPO . |
| 9623010 | of 1996 | WIPO . |
| 9633202 | of 1996 | WIPO . |
| 9702298 | of 1997 | WIPO . |
| 9745434 | 5/1997 | WIPO . |

OTHER PUBLICATIONS

Gibson et al. "Synthesis and structural characterisation of aluminum imino–amide . . . " J. Organomet. Chem. 550, 453–456, 1998. (Jan.), May 1998.
Fuhrmann et al., Inorg. Chem 1996, 35, 6742–6745 (Feb.).
Derwent Abstract 92–350947/43—Sumitomo Chem Co. Ltd.
Derwent Abstract 89–174462/24—Dow Chemical Co.
Chem. Commun., 1998 849–850 "Novel Olefin Polymerization Catalysts Based on Iron and Cobalt", George J.P. Britovsek et al. (May).
Journal of Organometallic Chemistry 550 (1998) 453–456 "Synthesis and Structural characterisation of aluminum . . . ", Gibson et al. (Jan.).
Organometalics 1997, 16, 1247–1252 "Lithium Derivatives of Novel Monoaniomic . . . " Deelman et al. (Aug).
Journal of Organometalic Chemistry 513 (1996) 281–285, "Novel monoanionic di–N,N'–centered chelating . . . " Deelman et al. (Nov.).
J. Chem. Soc., Chem. Commun. 1994 "Transformation of the Bis(trimethylsilyl)methyl into . . . " Hitchcock et al. 2637–2638 (Aug.).
J. Chem. Soc., Chem. Commun. 1994 "Transformation of the Bis(trimethylsilyl)methyl into . . . " Hitchcock et al. 1699–1700 (May).
Inorganica Chimica Acta. 166 (1989) 221–231 "Structural Investigations of the . . . " Clarke, et al. (Jun.).
Organometallics 1995, 14, 371–386 "Synthesis, Structures, and Reactivity . . . " Tjaden et al. (Jul.).
J. Chem. Soc. Dalton Trans. 1990 cis–and trans–Dichloro— derivatives . . . Corazza et al. 1335–1344 (Aug.).
Inorg. Chem 1995, 34, 2921–2930, "Oxazoline Early Transition Metal Complexes . . . " Cozzi et al. (Dec.).
Journal of Organometallic Chemistry 503 (1995) 307–314 "Bis(trimethylsilyl)benzamidinate . . . " Korine et al. (Mar.).
Journal of Organometallic Chemistry 491 (1995) 153–158 "Mono–η–cyclopentadienyl . . . " Gomez et al. (Aug.).
Organometallics 1995, 14, 1827–1833 "[N, N'–Bis(trimethylsily)benzamidinatol] . . . " Flores, et al. (Oct.).
Inorg. Chem. 1996, 35, 6546–6551 "N–Methyl–2–(methylamino)troponiminate . . . " Dias et al. (Jun.).
Polyhedron vol. 16 No. 3 pp. 541–550, 1997 "Structural Studies of formamidine compounds: . . . "'Cotton et al. (Apr.).
Organometallics 1994, 13, 4398–4405 "Coordination of the Bis(pyridyl)methyl . . . " Gornitzka et al. (May).
Chem. Ber 121, 1403–1406 (1988) "Benzamidnatokomplexe mit Haupt–. . . " Roesky et al. (Feb.).
J. Chem Soc. Dalton Trans 1995 25–30 "Zirconium Complexes incorporating . . . " Cloke et al. (Jul.).

(List continued on next page.)

*Primary Examiner*—Karl Group
*Assistant Examiner*—Michael J. DeVerdi
*Attorney, Agent, or Firm*—S. R. Bresch

[57] ABSTRACT

A catalyst precursor having the formula:

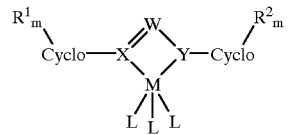

wherein M is a Group IVB metal;
  each L is a monovalent, bivalent, or trivalent anion;
  X and Y are each heteroatoms;
  each Cyclo is a cyclic moiety;
  each $R^1$ is a group containing 1 to 50 atoms selected from the group consisting of hydrogen and Group IIIA to Group VIIA elements, and two or more adjacent $R^1$ groups may be joined to form a cyclic moiety;
  each $R^2$ is a group containing 1 to 50 atoms selected from the group consisting of hydrogen and Group IIIA to Group VIIA elements, and two or more adjacent $R^2$ groups may be joined to form a cyclic moiety;
  W is a bridging group; and
  each m is independently an integer from 0 to 5.

10 Claims, No Drawings

OTHER PUBLICATIONS

J. Am. Chem. Soc. 1995, 117, 3008–3021 "Polymerization of α–Olefins and Butadiene . . . " Linden et al. (Jul.).

Angew. Chem. Int. Ed. Engl. 1994 33, No. 1 95–97 "Facile Reduction of a Dialkyl . . . " Brand et al. (Jul.).

Chem. Soc. Dalton Trans 1994 2015–2017 "Functionalizable 5,5,10,10,15,15,20,20 . . . " Solari et al. (Apr.).

J. Am. Chem. Soc. 1993, 115, 8493–8494 "Cationic $d^0$ Metal Alkyls . . . " Uhrhammer et al. (Apr.).

Angew. Chem Int. Ed. Engl. 1994, 33 No. 21 "Tetraaza[14]annulenezirconium(IV) . . . " Giannini, et al., (May).

J. Am. Chem Soc. 1994, 116, 4382–4390, "Synthesis of Molybdenum and Tungsten Complexes That . . . " Kol, et al. (Oct.).

Organometallics 1997, 16 3282–3302 "Synthesis, Structures, Bonding . . . " Bei et al. (Mar.).

Organometallics 1997, 16, 3303–3313 "Neutral and Cationic Zirconium . . . " Tsukahara, et al. (Mar.).

Organometallics 1997, 16, 3314–3323 "Synthesis, Structures, Dynamics, and Olefin . . . " Kim et al. (Mar.).

Durfee et al., *Organometallics,* vol. 9, No. 1, 1990, pp. 75 to 80, (Jan.).

Lappert et al., *Journal of Organometallics Chemistry,* 500, 1995, pp. 203 to 217, (Sep.).

CATALYST FOR THE PRODUCTION OF OLEFIN POLYMERS

This application claims the benefit of provisional U.S. Application Serial No. 60/051,522, filed Jul. 2, 1997, the disclosure of which is incorporated herein by reference.

The invention relates to a family of novel heteroatom-containing catalyst precursors useful for the polymerization of olefins, such as ethylene, higher alpha-olefins, dienes, and mixtures thereof.

BACKGROUND

A variety of metallocenes and other single site-like catalysts have been developed to prepare olefin polymers. Metallocenes are organometallic coordination complexes containing one or more π-bonded moieties (i.e., cyclopentadienyl groups) in association with a metal atom. Catalyst compositions containing metallocenes and other single site-like catalysts are highly useful in the preparation of polyolefins, producing relatively homogeneous copolymers at excellent polymerization rates while allowing one to tailor closely the final properties of the polymer as desired.

Recently, work relating to certain nitrogen-containing, single site-like catalyst precursors has been published. PCT Application No. WO 96/23101 relates to di(imine) metal complexes that are transition metal complexes of bidentate ligands selected from the group consisting of:

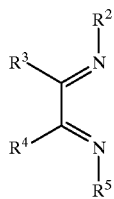

(V)

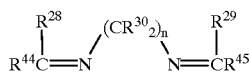

(VI)

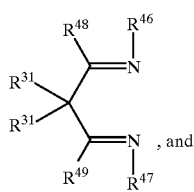

, and (VII)

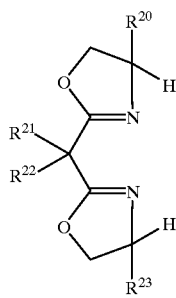

(VIII)

wherein said transition metal is selected from the group consisting of Ti, Zr, Sc, V, Cr, a rare earth metal, Fe, Co, Ni, and Pd;

$R^2$ and $R^5$ are each independently hydrocarbyl or substituted hydrocarbyl, provided that the carbon atom bound to the imino nitrogen atom has at least two carbon atoms bound to it;

$R^3$ and $R^4$ are each independently hydrogen, hydrocarbyl, substituted hydrocarbyl, or $R^3$ and $R^4$ taken together are hydrocarbylene or substituted hydrocarbylene to form a carbocyclic ring;

$R^{44}$ is hydrocarbyl or substituted hydrocarbyl, and $R^{28}$ is hydrogen, hydrocarbyl or substituted hydrocarbyl or $R^{44}$ and $R^{28}$ taken together form a ring;

$R^{45}$ is hydrocarbyl or substituted hydrocarbyl, and $R^{29}$ is hydrogen, substituted hydrocarbyl or hydrocarbyl, or $R^{45}$ and $R^{29}$ taken together form a ring;

each $R^{30}$ is independently hydrogen, substituted hydrocarbyl or hydrocarbyl, or two of $R^{30}$ taken together form a ring;

each $R^{31}$ is independently hydrogen, hydrocarbyl or substituted hydrocarbyl;

$R^{46}$ and $R^{47}$ are each independently hydrocarbyl or substituted hydrocarbyl, provided that the carbon atom bound to the imino nitrogen atom has at least two carbon atoms bound to it;

$R^{48}$ and $R^{49}$ are each independently hydrogen, hydrocarbyl, or substituted hydrocarbyl;

$R^{20}$ and $R^{23}$ are independently hydrocarbyl or substituted hydrocarbyl;

$R^{21}$ and $R^{22}$ are independently hydrogen, hydrocarbyl or substituted hydrocarbyl; and n is 2 or 3;

and provided that:

said transition metal also has bonded to it a ligand that may be displaced by or added to the olefin monomer being polymerized; and when the transition metal is Pd, said bidentate ligand is (V), (VII) or (VIII).

An olefin polymerization catalyst composition is described herein having good polymerization activity and productivity. The catalyst composition comprises a heteroatom-containing catalyst precursor having the formula:

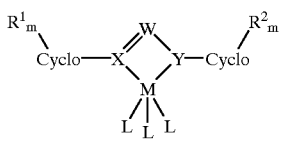

wherein M is a Group IVB metal;

each L is a monovalent, bivalent, or trivalent anion;

X and Y are each heteroatoms;

each Cyclo is a cyclic moiety;

each $R^1$ is a group containing 1 to 50 atoms selected from the group consisting of hydrogen and Group IIIA to Group VIIA elements, and two or more adjacent $R^1$ groups may be joined to form a cyclic moiety;

each $R^2$ is a group containing 1 to 50 atoms selected from the group consisting of hydrogen and Group IIIA to Group VIIA elements, and two or more adjacent $R^2$ groups may be joined to form a cyclic moiety;

W is a bridging group; and each m is independently an integer from 0 to 5.

The catalyst precursor may be conveniently prepared by reacting a Group IVB organometal compound with a heteroatom-containing ligand of the formula:

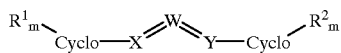

wherein X, Y, W, Cyclo, $R^1$, $R^2$, and m have the meanings stated above.

SUMMARY OF THE INVENTION

The invention provides a catalyst precursor of the formula:

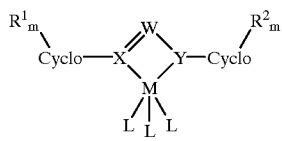

wherein M is a Group IVB metal;
each L is a monovalent, bivalent, or trivalent anion;
X and Y are each heteroatoms;
each Cyclo is a cyclic moiety;
each $R^1$ is a group containing 1 to 50 atoms selected from the group consisting of hydrogen and Group IIIA to Group VIIA elements, and two or more adjacent $R^1$ groups may be joined to form a cyclic moiety;
each $R^2$ is a group containing 1 to 50 atoms selected from the group consisting of hydrogen and Group IIIA to Group VIIA elements and two or more adjacent $R^2$ groups may be joined to form a cyclic moiety;
W is a bridging group; and
each m is independently an integer from 0 to 5;
along with a catalyst composition comprising this catalyst precursor and an activating cocatalyst, as well as a process for the polymerization of olefins using this catalyst composition.

The invention also provides a catalyst precursor comprising the reaction product of a Group IVB organometal compound and heteroatom-containing ligand having the formula:

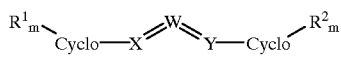

wherein X and Y are each heteroatoms;
each Cyclo is a cyclic moiety;
each $R^1$ is a group containing 1 to 50 atoms selected from the group consisting of hydrogen and Group IIIA to Group VIIA elements and two or more adjacent $R^1$ groups may be joined to form a cyclic moiety;
each $R^2$ is a group containing 1 to 50 atoms selected from the group consisting of hydrogen and Group IIIA to Group VIIA elements and two or more adjacent $R^2$ groups may be joined to form a cyclic moiety;
W is a bridging group; and
each m is independently an integer from 0 to 5;
as well as a catalyst composition comprising this catalyst precursor and an activating cocatalyst, and a process for polymerizing olefins using this catalyst composition.

DETAILED DESCRIPTION OF THE INVENTION

The catalyst precursor may have the formula:

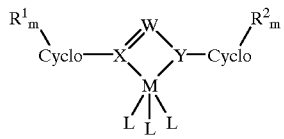

In the above formula, M is a Group IVB metal, preferably zirconium.

Each L is a monovalent, bivalent, or trivalent anion, preferably independently selected from the group consisting of halogens; hydrogen; alkyl, aryl, alkenyl, alkylaryl, arylalkyl, or hydrocarboxy radicals having 1–20 carbon atoms; amides; phosphides; sulfides; silylalkyls; diketonates; and carboxylates. More preferably, each L is selected from the group consisting of halides, alkyl radicals, and arylalkyl radicals. Most preferably, each L is selected from the group consisting of arylalkyl radicals such as benzyl. Each L may contain one or more heteroatoms.

X and Y are each heteroatoms and are preferably independently selected from the group consisting of N, O, S, and P. More preferably, X and Y are independently selected from the group consisting of N and P. Most preferably, X and Y are both nitrogen.

Each Cyclo is a cyclic moiety. Preferably, each Cyclo is a carbocyclic ring containing 3 to 7 carbon atoms. More preferably, each Cyclo is an aryl group.

Each $R^1$ is a group containing 1 to 50 atoms selected from the group consisting of hydrogen and Group IIIA to Group VIIA elements, and two or more adjacent $R^1$ groups may be joined to form a cyclic moiety such as an aliphatic or aromatic ring. Preferably, $R^1$ is an alkyl. More preferably, $R^1$ is isopropyl. Optionally, an $R^1$ group may be joined to W.

Each $R^2$ is a group containing 1 to 50 atoms selected from the group consisting of hydrogen and Group IIIA to Group VIIA elements and two or more adjacent $R^2$ groups may be joined to form a cyclic moiety such as an aliphatic or aromatic ring. Preferably, $R^2$ is hydrogen or an aryl. More preferably, $R^2$ is hydrogen. Optionally, an $R^2$ group may be joined to W.

W is a bridging group. Preferably, W contains one or more Group IIIA, Group IVA, Group VA, or Group VIA elements. More preferably, W contains one or more Group IVA elements. Most preferably, W is a two carbon bridge wherein each carbon is substituted with a methyl group.

Each m is independently an integer from 0 to 5, preferably 2.

In a preferred embodiment of the invention, the catalyst precursor has the formula:

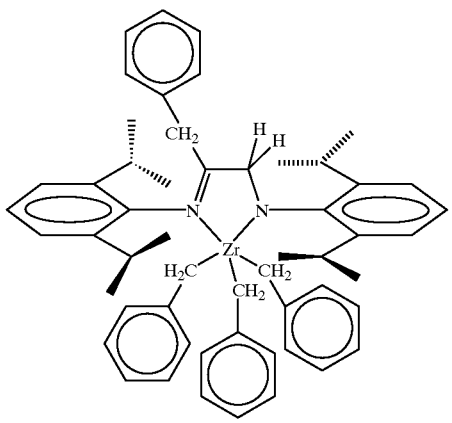

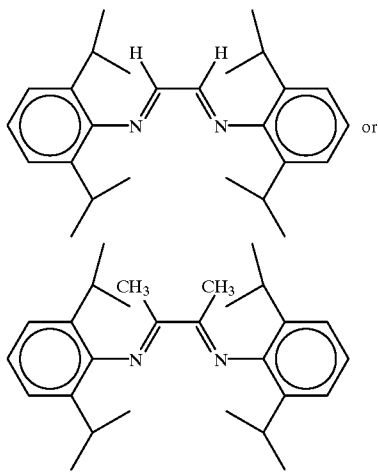

The catalyst precursor may be made by any method. The method of making the catalyst precursor is not critical to the invention. However, one useful method of making the catalyst precursor is by reacting a Group IVB organometal compound with a heteroatom-containing ligand.

The Group IVB organometal compound for example may be a Group IVB metal alkyl, aryl, arylalkyl, silylalkyl, amide, or phosphide. Preferably, the Group IVB organometal compound is a Group IVB metal alkyl, arylalkyl, or aryl. More preferably, the Group IVB organometal compound is a Group IVB metal arylalkyl.

Examples of useful Group IVB organometal compounds are tetramethylzirconium, tetraethylzirconium, tetrakis[trimethylsilylmethyl]zirconium, tetrakis[dimethylamino]zirconium, dichlorodibenzylzirconium, chlorotribenzylzirconium, trichlorobenzylzirconium, bis[dimethylamino]bis[benzyl]zirconium, and tetrabenzylzirconium.

Tetramethyltitanium, tetraethyltitanium, tetrakis[trimethylsilylmethyl]titanium, tetrakis[dimethylamino]titanium, dichlorodibenzyltitanium, chlorotribenzyltitanium, trichlorobenzyltitanium, bis[dimethylamino]bis[benzyl]titanium, and tetrabenzyltitanium.

Tetramethylhafnium, tetraethylhafnium, tetrakis[trimethylsilylmethyl]hafnium, tetrakis[dimethylamino]hafnium, dichlorodibenzylhafnium, chlorotribenzylhafnium, trichlorobenzylhafnium, bis[dimethylamino]bis[benzyl]hafnium, and tetrabenzylhafnium.

Preferably, the Group IVB organometal compound is an zirconium hydrocarbyl. More preferably, the Group IVB organometal compound is a zirconium arylalkyl. Most preferably, the Group IVB organometal compound is tetrabenzylzirconium.

The heteroatom-containing ligand has the formula:

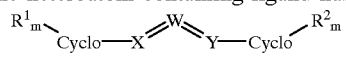

wherein X, Y, W, Cyclo, $R^1$, $R^2$, and m have the meanings stated above. Preferably, the heteroatom-containing ligand is a diazabutadiene ligand of the formula:

For example, the preferred catalyst precursor

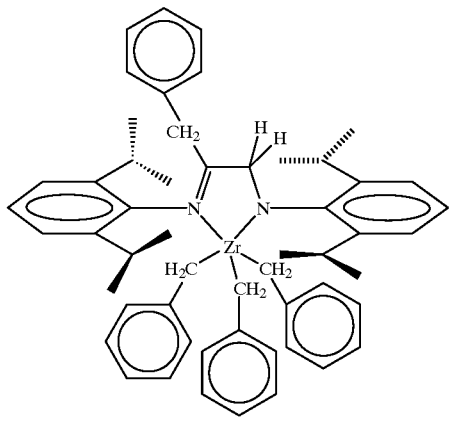

may be made by reacting a diazabutadiene ligand with a zirconium arylalkyl such as tetrabenzyl zirconium:

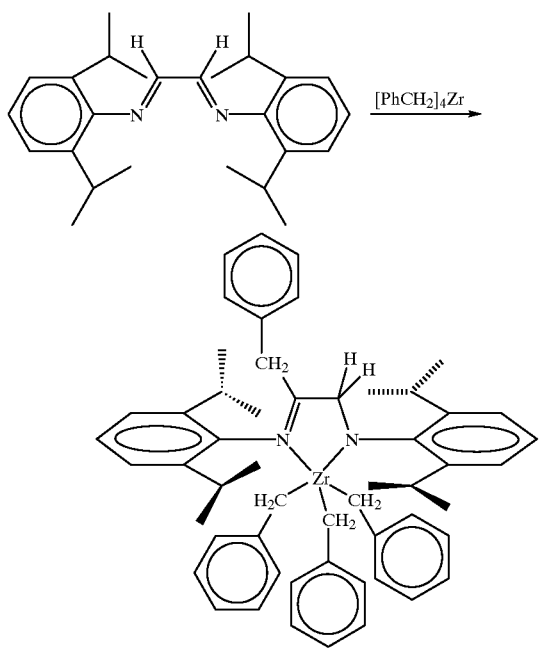

This reaction is preferably carried out in a suitable solvent such as toluene or benzene at a temperature in the range of −50 to 50° C. and a pressure ranging from a vacuum to 1000 psi.

Alternatively, the catalyst precursor can be made by reacting the heteroatom-containing ligand with a metal halide and then further reacting the product thereof with a Grignard reagent, such as an organomagnesium halide. For instance, the same catalyst precursor

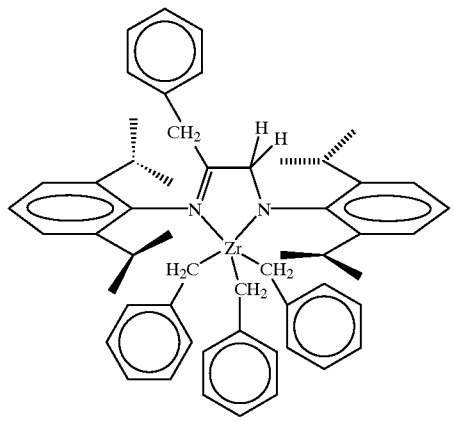

may be made by reacting a diazabutadiene ligand with a zirconium halide such as zirconium tetrachloride, and then further reacting the product thereof with PhCH₂MgCl.

The catalyst precursor may be isolated by conventional methods.

The catalyst composition comprises the catalyst precursor and an activating cocatalyst. The activating cocatalyst is capable of activating the catalyst precursor. Preferably, the activating cocatalyst is one of the following: (a) branched or cyclic oligomeric poly(hydrocarbylaluminum oxide)s which contain repeating units of the general formula —(Al(R*)O)—, where R* is hydrogen, an alkyl radical containing from 1 to about 12 carbon atoms, or an aryl radical such as a substituted or unsubstituted phenyl or naphthyl group; (b) ionic salts of the general formula $[A^+][BR^{}_4{}^-]$, where $A^+$ is a cationic Lewis or Bronsted acid capable of abstracting an alkyl, halogen, or hydrogen from the metallocene catalysts, B is boron, and R is a substituted aromatic hydrocarbon, preferably a perfluorophenyl radical; (c) boron alkyls of the general formula $BR^{}_3$, where R is as defined above; or mixtures thereof.

Preferably, the activating cocatalyst is a branched or cyclic oligomeric poly(hydrocarbylaluminum oxide) or a boron alkyl. More preferably, the activating cocatalyst is an aluminoxane such as methylaluminoxane (MAO) or modified methylaluminoxane (MMAO), or a boron alkyl.

Aluminoxanes are well known in the art and comprise oligomeric linear alkyl aluminoxanes represented by the formula:

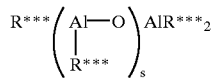

and oligomeric cyclic alkyl aluminoxanes of the formula:

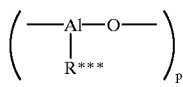

wherein s is 1–40, preferably 10–20; p is 3–40, preferably 3–20; and R*** is an alkyl group containing 1 to 12 carbon atoms, preferably methyl.

Aluminoxanes may be prepared in a variety of ways. Generally, a mixture of linear and cyclic aluminoxanes is obtained in the preparation of aluminoxanes from, for example, trimethylaluminum and water. For example, an aluminum alkyl may be treated with water in the form of a moist solvent. Alternatively, an aluminum alkyl, such as trimethylaluminum, may be contacted with a hydrated salt, such as hydrated ferrous sulfate. The latter method comprises treating a dilute solution of trimethylaluminum in, for example, toluene with a suspension of ferrous sulfate heptahydrate. It is also possible to form methylaluminoxanes by the reaction of a tetraalkyldialuminoxane containing $C_2$ or higher alkyl groups with an amount of trimethylaluminum that is less than a stoichiometric excess. The synthesis of methylaluminoxanes may also be achieved by the reaction of a trialkyl aluminum compound or a tetraalkyldialuminoxane containing $C_2$ or higher alkyl groups with water to form a polyalkyl aluminoxane, which is then reacted with trimethylaluminum. Further modified methylaluminoxanes, which contain both methyl groups and higher alkyl groups, i.e., isobutyl groups, may be synthesized by the reaction of a polyalkyl aluminoxane containing $C_2$ or higher alkyl groups with trimethylaluminum and then with water as disclosed in, for example, U.S. Pat. No. 5,041,584.

When the activating cocatalyst is a branched or cyclic oligomeric poly(hydrocarbylaluminum oxide), the mole ratio of aluminum atoms contained in the poly (hydrocarbylaluminum oxide) to total metal atoms contained in the catalyst precursor is generally in the range of from about 2:1 to about 100,000:1, preferably in the range of from about 10:1 to about 10,000:1, and most preferably in the range of from about 50:1 to about 2,000:1. When the activating cocatalyst is an ionic salt of the formula $[A^+][BR^{}_4{}^-]$ or a boron alkyl of the formula $BR^{}_3$, the mole ratio of boron atoms contained in the ionic salt or the boron alkyl to total metal atoms contained in the catalyst precursor is generally in the range of from about 0.5:1 to about 10:1, preferably in the range of from about 1:1 to about 5:1.

The catalyst precursor, the activating cocatalyst, or the entire catalyst composition may be impregnated onto a solid, inert support, in liquid form such as a solution, dispersion or neat liquid, spray dried, in the form of a prepolymer, or formed in-situ during polymerization. Particularly preferred among these is a catalyst composition that is spray dried as described in European Patent Application No. 0 668 295 A1 or in liquid form as described in U.S. Pat. No. 5,317,036.

In the case of a supported catalyst composition, the catalyst composition may be impregnated in or deposited on the surface of an inert substrate such as silica, carbon black, polyethylene, polycarbonate porous crosslinked polystyrene, porous crosslinked polypropylene, alumina, thoria, zirconia, or magnesium halide (e.g., magnesium dichloride), such that the catalyst composition is between 0.1 and 90 percent by weight of the total weight of the catalyst composition and the support.

The catalyst composition may be used for the polymerization of olefins by any suspension, solution, slurry, or gas phase process, using known equipment and reaction conditions, and is not limited to any specific type of reaction system. Generally, olefin polymerization temperatures range from about 0° C. to about 200° C. at atmospheric, subatmospheric, or superatmospheric pressures. Slurry or solution polymerization processes may utilize subatmospheric or superatmospheric pressures and temperatures in the range of about 40° C. to about 110° C. A useful liquid phase polymerization reaction system is described in U.S. Pat. No. 3,324,095. Liquid phase reaction systems generally comprise a reactor vessel to which olefin monomer and catalyst composition are added, and which contains a liquid reaction medium for dissolving or suspending the polyolefin. The liquid reaction medium may consist of the bulk liquid monomer or an inert liquid hydrocarbon that is nonreactive under the polymerization conditions employed. Although such an inert liquid hydrocarbon need not function as a solvent for the catalyst composition or the polymer obtained by the process, it usually serves as solvent for the monomers employed in the polymerization. Among the inert liquid hydrocarbons suitable for this purpose are isopentane, hexane, cyclohexane, heptane, benzene, toluene, and the like. Reactive contact between the olefin monomer and the catalyst composition should be maintained by constant stirring or agitation. The reaction medium containing the olefin polymer product and unreacted olefin monomer is withdrawn from the reactor continuously. The olefin polymer product is separated, and the unreacted olefin monomer and liquid reaction medium are recycled into the reactor.

Preferably, gas phase polymerization is employed, with superatmospheric pressures in the range of 1 to 1000 psi, preferably 50 to 400 psi, most preferably 100 to 300 psi, and temperatures in the range of 30 to 130° C., preferably 65 to 110° C. Stirred or fluidized bed gas phase reaction systems are particularly useful. Generally, a conventional gas phase, fluidized bed process is conducted by passing a stream containing one or more olefin monomers continuously through a fluidized bed reactor under reaction conditions and in the presence of catalyst composition at a velocity sufficient to maintain a bed of solid particles in a suspended condition. A stream containing unreacted monomer is withdrawn from the reactor continuously, compressed, cooled, optionally fully or partially condensed as disclosed in U.S. Pat. Nos. 4,528,790 and 5,462,999, and recycled to the reactor. Product is withdrawn from the reactor and make-up monomer is added to the recycle stream. As desired for temperature control of the system, any gas inert to the catalyst composition and reactants may also be present in the gas stream. In addition, a fluidization aid such as carbon black, silica, clay, or talc may be used, as disclosed in U.S. Pat. No. 4,994,534.

Polymerization may be carried out in a single reactor or in two or more reactors in series, and is conducted substantially in the absence of catalyst poisons. Organometallic compounds may be employed as scavenging agents for poisons to increase the catalyst activity. Examples of scavenging agents are metal alkyls, preferably aluminum alkyls, most preferably triisobutylaluminum.

Conventional adjuvants may be included in the process, provided they do not interfere with the operation of the catalyst composition in forming the desired polyolefin. Hydrogen or a metal or non-metal hydride, e.g., a silyl hydride, may be used as a chain transfer agent in the process. Hydrogen may be used in amounts up to about 10 moles of hydrogen per mole of total monomer feed.

Olefin polymers that may be produced according to the invention include, but are not limited to, ethylene homopolymers, homopolymers of linear or branched higher alpha-olefins containing 3 to about 20 carbon atoms, and interpolymers of ethylene and such higher alpha-olefins, with densities ranging from about 0.86 to about 0.96. Suitable higher alpha-olefins include, for example, propylene, 1-butene, 1-pentene, 1-hexene, 4-methyl-1-pentene, 1-octene, and 3,5,5-trimethyl-1-hexene. Olefin polymers according to the invention may also be based on or contain conjugated or non-conjugated dienes, such as linear, branched, or cyclic hydrocarbon dienes having from about 4 to about 20, preferably 4 to 12, carbon atoms. Preferred dienes include 1,4-pentadiene, 1,5-hexadiene, 5-vinyl-2-norbornene, 1,7-octadiene, vinyl cyclohexene, dicyclopentadiene, butadiene, isobutylene, isoprene, ethylidene norbornene and the like. Aromatic compounds having vinyl unsaturation such as styrene and substituted styrenes, and polar vinyl monomers such as acrylonitrile, maleic acid esters, vinyl acetate, acrylate esters, methacrylate esters, vinyl trialkyl silanes and the like may be polymerized according to the invention as well. Specific olefin polymers that may be made according to the invention include, for example, polyethylene, polypropylene, ethylene/propylene rubbers (EPR's), ethylene/propylene/diene terpolymers (EPDM's), polybutadiene, polyisoprene and the like.

The following examples further illustrate the invention.

EXAMPLES

Glossary

Activity is measured in g polyethylene/mmol metal.hr.100 psi ethylene.

I21 is flow index (dg/min) as measured by ASTM D-1238.

BBF is butyl branch frequency per 1000 main chain carbon atoms based on infrared measurement techniques.

Example 1

Preparation of Glyoxal-Bis(2,6-Diisopropylphenylimine) Ligand

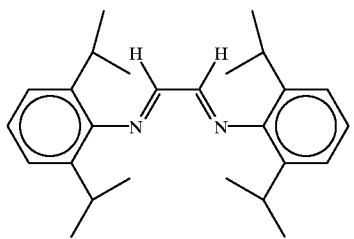

Into a 300 mL three neck flask equipped with a stir bar and sealed with septa, was charged 100 mmol (17.73 g) 2,6-diisopropylaniline. 100 mL methanol was added and stirred to dissolve. The pale pink solution was chilled to 0° C. and approximately 5 mole % (0.19 mL) formic acid was added dropwise while stirring. The solution was allowed to warm to room temperature and 50 mmol (7.25 mL) glyoxal (40 wt % in water) was added dropwise while stirring. The solution turned light yellow-orange. Yellow solids began precipitating from the dark orange solution after 1 hour. The reaction was allowed to run overnight.

The crude product was filtered from the solvent using a 150 mL medium porosity frit. The solids were washed with cold methanol, then placed in a 500 mL Erlenmyer flask equipped with a stir bar. Approximately 100 mL hexane was added to dissolve solids and sufficient Na$_2$SO$_4$ was added to complete drying of solution. The vessel was sealed with a septa and allowed to stir 6 hours.

The Na$_2$SO$_4$ was filtered from the solution using a 150 mL medium porosity frit. The filtrate was collected in a Schlenk flask equipped with a stir bar and vacuum stripped (0.5 Torr). To the bright yellow powdery residue was added 50 mL methanol. This was heated to 63° C. and while stirring hexane was added in 5 mL increments (for a total of 25 mL) until all the product was dissolved. The solution was then allowed to cool and stand overnight. The solids were filtered from the solvent using a 150 mL medium porosity frit. The solids were dried under high vacuum (0.5 Torr). Total product collected was 10.8 g (57% yield).

Example 2

Reaction of Tetrabenzylzirconium and Glyoxal-Bis(2,6-Diisopropylphenylimine)

To an oven-dried round bottom flask was charged neat 1.3 mmoles of the ligand of Example 1 and 1.3 mmoles of tetrabenzylzirconium in the dry box. 1.0 ml of dry benzene-d6 was added; and the mixture was allowed to stir overnight in the absence of light. The mixture was then filtered through an oven-dried medium frit. The solids (0.63 g) were collected and dissolved in generous amounts of dry toluene. This was done by adding the toluene in portions followed by swirling. Once dissolved the solution was poured into an oven-dried Schlenck tube wrapped in aluminum foil. An oven-dried syringe and 25 gauge needle were then used to layer a thin stream of dry hexane gently on top of the toluene solution. Five times the amount of dry hexane was layered on top of the toluene solution. The Schlenck tube was stoppered and examined periodically for crystal growth. Six days later crystals could be seen on the sides of the Schlenck tube directly beneath the toluene/hexane interface. Over the next few days the amount of crystals had increased. On day twelve the solvent was removed via a syringe and concentrated invacuo. The crystals remained in the Schlenck tube and were guarded against light.

Example 3

A series of ethylene polymers were made in a laboratory scale, slurry phase reactor using catalyst compositions according to the invention. Each polymerization reaction was conducted in n-hexane (607 mL) with 43 mL of 1-hexene (alumina and de-oxo treated) as comonomer.

The catalyst compositions were prepared by mixing 0.1 mL of 1-hexene, a solution of Catalyst Precursor A or B in benzene d6, and modified methylaluminoxane (MMAO, 7.0 wt % Al in heptane, commercially available from Akzo Chemicals, Inc.) to arrive at Al/Zr mole ratios of 1000/1. Catalyst Precursors A and B were made by the reaction of Ligand A and B, respectively, with tetrabenzylzirconium.

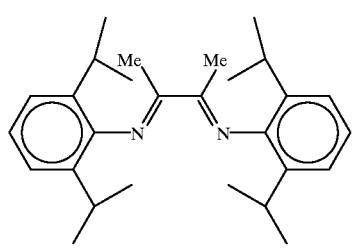

Ligand A

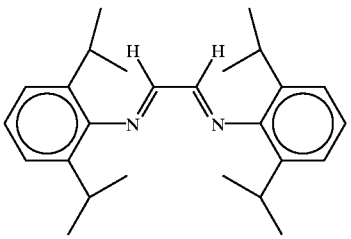

Ligand B

Reaction conditions and results are shown in Table 1 below.

TABLE 1

| Example | Ligand | μmol of Zr | T, ° C. | C2 psi | Activity | Mn | Mw | PDI |
|---|---|---|---|---|---|---|---|---|
| 3a | A | 1.8 | 65° C. | 85 | 43,529 | NA | NA | — |
| 3b | A | 1.8 | 75° C. | 85 | 15,686 | 9,534 | 185K | 19.43 |
| 3c | A | 1.8 | 65° C. | 200 | 34,000* | NA | NA | — |
| 3d | B | 9.0 | 65° C. | 85 | 4863 | 5,332 | 61K | 11.46 |

*Trouble controlling the reaction.

Example 4

A series of ethylene polymers were made in a laboratory scale, slurry phase reactor using catalyst compositions according to the invention.

The catalyst compositions were prepared by mixing 0.1 mL of 1-hexene, a solution of catalyst precursor in benzene d6, and MMAO (7.0 wt % Al in heptane, commercially available from Akzo Chemicals, Inc.). Al/Zr mole ratios were 1000/1. Catalyst precursors were made by reacting ligands of the formula below, wherein $R^1$, $R^2$, and $R^3$ are defined in Table 2, with tetrabenzylzirconium. Table 2 also shows the reaction conditions and results.

TABLE 2

| Example | $R_1$ | $R_2$ | $R_3$ | Activity |
|---|---|---|---|---|
| 4a | Me | Me | Me | 18,431 |
| 4b | Me | Me | H | 3,399 |
| 4c | Me | i-Pr | Me | 32,810 |
| 4d | Me | i-Pr | H | 2,118 |
| 4e | H | H | Me | 10,965 |
| Comparative 1 | No Ligand Added | | | 784 |

Example 5

Two ethylene polymers were made in a laboratory scale, slurry phase reactor using catalyst compositions according to the invention.

The catalyst compositions were prepared by mixing 0.1 mL of 1-hexene, a solution of catalyst precursor in benzene d6, and MMAO (7.0 wt % Al in heptane, commercially available from Akzo Chemicals, Inc.). Catalyst precursors were made by reacting ligands of the formula below, wherein R is defined in Table 3, with tetrabenzylzirconium. Table 3 also shows the reaction conditions and results.

TABLE 3

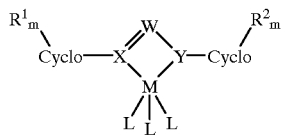

| Example | R | Activity |
|---------|---|----------|
| 5a | Me | 424 |
| 5b | H | 3,629 |

Example 6

An ethylene polymer was made in a laboratory scale, slurry phase reactor using a catalyst composition of the invention comprising MMAO (7.0 wt.% Al in heptane, commercially available from Akzo Chemicals, Inc.) and a catalyst precursor made by reacting tetrabenzylzirconium with:

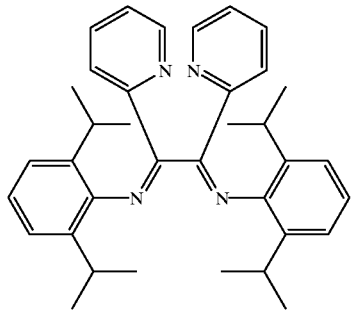

23.7 grams of polyethylene were made, and the catalyst composition activity was 5,414.

Example 7

The catalyst compositions of Example 3 are used to make polyethylene in a pilot-scale, fluidized bed, gas phase reactor. The reactor is nominally 1 foot in diameter and is operated with a bed height of 8 feet and a superficial gas velocity of approximately 1.8 ft/sec. Total reactor pressure is 350 psig.

First, a seed bed is charged to the reactor and it was dried to <5 ppm water. The reactor is pressurized to 200 psig of ethylene. 1-Hexene and hydrogen levels in the reactor are adjusted as desired. The bed temperature is adjusted to 70° C.

Next, the catalyst composition is sprayed in liquid form into the reactor with the aid of 5.0–7.0 lb/hr of nitrogen gas and a stream of 1950 lbs/hr of recycle gas.

Polyethylene is produced.

I claim:

1. A catalyst precursor having the formula:

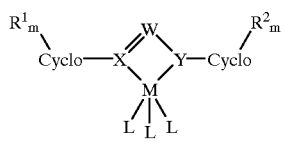

wherein M is a Group IVB metal;
   each L is a monovalent, bivalent or trivalent anion;
   X and Y are each heteroatoms;
   each Cyclo is a cyclic moiety;
   each R1 is a hydrocarbon group containing 1 to 50 atoms selected from the group consisting of hydrogen and Group IIIA to Group VIIA elements and two or more adjacent R1 groups may be joined to form a cyclic moiety;
   each R2 is a group containing 1 to 50 atoms selected from the group consisting of hydrogen and Group IIIA to Group VIIA elements and two or more adjacent R2 groups may be joined to form a cyclic moiety;
   W is a bridging group having two atoms and X and Y are not bound to the same atom of the bridging group; and
   each m is independently an integer from 0 to 5.

2. A catalyst precursor having the formula:

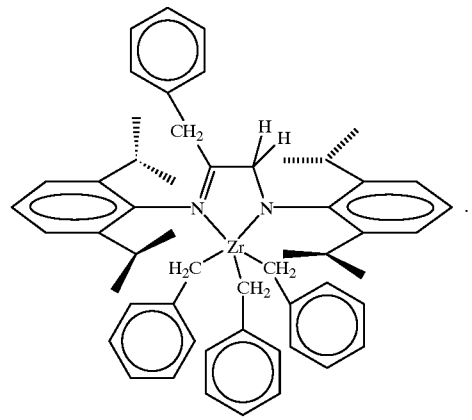

3. A catalyst composition comprising:
   a) a catalyst precursor having the formula

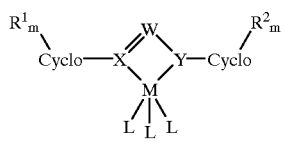

wherein M is a Group IVB metal;
   each L is a monovalent, bivalent or trivalent anion;
   X and Y are each heteroatoms;
   each Cyclo is a cyclic moiety;
   each R1 is a group containing 1 to 50 atoms selected from the group consisting of hydrogen and Group IIIA to Group VIIA elements and two or more adjacent R1 groups may be joined to form a cyclic moiety;
   each R2 is a group containing 1 to 50 atoms selected from the group consisting of hydrogen and Group IIIA to Group VIIA elements and two or more adjacent R2 groups may be joined to form a cyclic moiety;

W is a bridging group having at least two atoms and X and Y are not bound to the same atom of the bridging group; and each m is independently an integer from 0 to 5; and b) an activating cocatalyst.

4. The catalyst composition of claim 3, wherein the catalyst precursor has the formula:

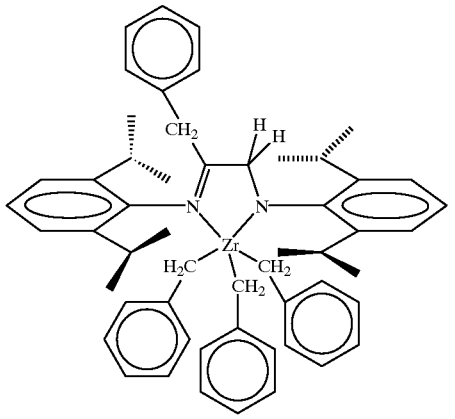

5. The catalyst composition of claim 3 in liquid form.

6. A catalyst precursor comprising the reaction product of a Group IVB organometal compound and a heteroatom-containing ligand having the formula:

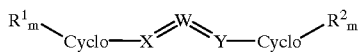

wherein X and Y are each heteroatoms;

each Cyclo is a cyclic moiety;

each R1 is a group containing 1 to 50 atoms selected from the group consisting of hydrogen and Group IIIA to Group VIIA elements and two or more adjacent R1 groups may be joined to form a cyclic moiety;

each R2 is a group containing 1 to 50 atoms selected from the group consisting of hydrogen and Group IIIA to Group VIIA elements and two or more adjacent R2 groups may be joined to form a cyclic moiety;

W is a bridging group having at least two atoms and X and Y are not bound to the same atom of the bridging group; and each m is independently an integer from 0 to 5.

7. The catalyst precursor of claim 6, wherein the organometal compound is a zirconium hydrocarbyl and the heteroatom-containing ligand has the formula:

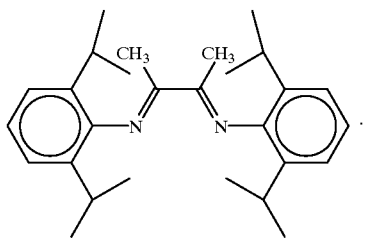

8. A catalyst composition comprising:

a) a catalyst precursor that is the reaction product of a Group IVB organometal compound and a heteroatom-containing ligand having the formula:

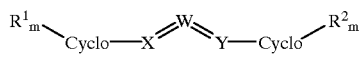

wherein X and Y are each heteroatoms;

each Cyclo is a cyclic moiety;

each R1 is a group containing 1 to 50 atoms selected from the group consisting of hydrogen and Group IIIA to Group VIIA elements, and two or more adjacent R1 groups may be joined to form a cyclic moiety;

each R2 is a hydrocarbon group containing 1 to 50 atoms selected from the group consisting of hydrogen and Group IIIA to Group VIIA elements, and two or more adjacent R2 groups may be joined to form a cyclic moiety;

W is a bridging group having at least two atoms and X and Y are not bound to the same atom of the bridging group; and each m is independently an integer from 0 to 5; and b) an activating cocatalyst.

9. The catalyst composition of claim 8, wherein the catalyst precursor comprises the reaction product of a zirconium hydrocarbyl and a ligand of the formula:

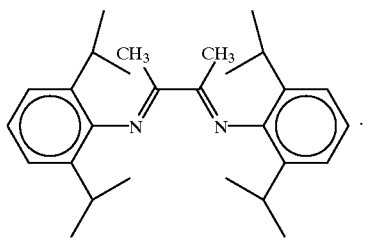

10. The catalyst composition of claim 8 in liquid form.

* * * * *